US010300053B2

(12) United States Patent
Eriksson et al.

(10) Patent No.: US 10,300,053 B2
(45) Date of Patent: May 28, 2019

(54) QUINOLINE CARBOXAMIDES FOR USE IN THE TREATMENT OF LEUKEMIA

(71) Applicant: Active Biotech AB, Lund (SE)

(72) Inventors: Helena Eriksson, Torna-Hällestad (SE); Leif Svensson, Rydebäck (SE); Marie Törngren, Genarp (SE)

(73) Assignee: ACTIVE BIOTECH AB, Lund (SE)

( * ) Notice: Subject to any disclaimer, the term of this patent is extended or adjusted under 35 U.S.C. 154(b) by 0 days.

(21) Appl. No.: 15/525,086

(22) PCT Filed: Nov. 5, 2015

(86) PCT No.: PCT/EP2015/075769
§ 371 (c)(1),
(2) Date: May 8, 2017

(87) PCT Pub. No.: WO2016/078921
PCT Pub. Date: May 26, 2016

(65) Prior Publication Data
US 2017/0319568 A1    Nov. 9, 2017

(30) Foreign Application Priority Data

Nov. 19, 2014   (EP) ..................................... 14193776

(51) Int. Cl.
*A61K 31/4704* (2006.01)
*A61K 9/20* (2006.01)

(52) U.S. Cl.
CPC ............ *A61K 31/4704* (2013.01); *A61K 9/20* (2013.01)

(58) Field of Classification Search
CPC .................................................. A61K 31/4704
USPC ....................................................... 514/299
See application file for complete search history.

(56) References Cited

FOREIGN PATENT DOCUMENTS

| EP | 2 537 517 A1 | 12/2012 | |
|---|---|---|---|
| WO | 1999/055678 A1 | 11/1999 | |
| WO | 2000/003991 A1 | 1/2000 | |
| WO | 2001/030758 A1 | 5/2001 | |
| WO | 2003/106424 A1 | 12/2003 | |
| WO | 2005/074899 A2 | 8/2005 | |
| WO | 2012/004338 A1 | 1/2012 | |
| WO | 2012/175541 A1 | 12/2012 | |
| WO | WO 2012/175541 | * 12/2012 | |
| WO | 2015/095833 A1 | 6/2015 | |

OTHER PUBLICATIONS

International Search Report for corresponding International Application No. PCT/SE2015/075769 dated Feb. 1, 2016.
Written Opinion of the International Search Authority for corresponding International Application No. PCT/SE2015/075769 dated Feb. 1, 2016.
International Preliminary Report on Patentability for corresponding International Application No. PCT/SE2015/075769 dated Feb. 27, 2017.
Bacher et al., "Recent advances in diagnosis, molecular pathology and therapy of chronic myelomonocytic leukaemia", British Journal of Haematology, vol. 153, No. 2, Apr. 1, 2011, pp. 149-167.
Isaacs et al., "Identification of ABR-215050 as Lead Second Generation Quinoline-3-Carboxamide Anti-Angiogenic Agent for the Treatment of Prostrate Cancer", The Prostate, vol. 66, 2006, pp. 1768-1778.
Joyce et al., "Microenvironmental regulation of metastasis", Nature Reviews Cancer, vol. 9, Apr. 2009, pp. 239-252.
Lettermann et al., "In Vivo RNAi Screening Identifies HDAC4 As a Mediator of Chemoresistance in Acute Myeloid Leukemia", Blood Journal, vol. 122, No. 21, Nov. 15, 2013, 1 page.
Parfenov et al., "Biotic Type Antioxidants: The Prospective Search Area for Novel Chemical Drugs", 2000, VSP BV, ISBN 90-6764-308-4.
Quintas-Cardama et al., "Histone deacetylase inhibitors for the treatment of myelodysplastic syndrome and acute myeloid leukemia", Nature, Leukemia, vol. 25, No. 2, Nov. 30, 2010, pp. 226-235.
Raymond et al., "Mechanisms of action of tasquinimod on the tumour microenvironment", Cancer Chemotherapy and Pharmacology, vol. 73, No. 1, Oct. 27, 2013, pp. 1-8.
Rowe et al., "Treatment of chronic myelogenous leukemia with autologous bone marrow transplantation followed by requinimex", Bone Marrow Transplantation, vol. 24, No. 10, Nov. 1, 1999, pp. 1057-1063.
Showel et al., "Advances in treating acute myeloid leukemia", F1000Prime Reports, 6:96, Oct. 1, 2014, pp. 1-9.
Simonsson et al., "Roquinimex (Linomide) vs placebo in AML after autologous bone marrow transplantation", Nature, Bone Marrow Transplantation, vol. 25, Jun. 1, 2000, pp. 1121-1127.
Weiss et al., "Linomide administration following bone marrow transplantation in mice", Cancer Immunol Immunother, vol. 51, 2002, pp. 595-602.

* cited by examiner

*Primary Examiner* — Rei Tsang Shiao
(74) *Attorney, Agent, or Firm* — Renner, Otto, Boisselle & Sklar, LLP

(57) ABSTRACT

A compound of formula (I) or a pharmaceutically acceptable salt thereof, for use in the treatment of leukemia.

18 Claims, 2 Drawing Sheets

QUINOLINE CARBOXAMIDES FOR USE IN THE TREATMENT OF LEUKEMIA

This application is a national phase of International Application No. PCT/EP2015/075769 filed Nov. 5, 2015 and published in the English language, and claims priority to EP 14193776.3 filed Nov. 19, 2014.

FIELD OF THE INVENTION

The present invention relates to certain quinoline carboxamides for use in the treatment of leukemia. More particularly, the invention relates to the compound 4-hydroxy-5-methoxy-N,1-dimethyl-2-oxo-N-[4-(trifluoromethyl) phenyl]-1,2-dihydroquinoline-3-carboxamide (tasquinimod), or a pharmaceutically acceptable salt thereof, for use in the treatment of leukemia.

BACKGROUND OF THE INVENTION

Various therapeutically active quinoline carboxamides and a method for their preparation were described in International Applications No. PCT/SE99/00676, published as WO 99/55678 and No. PCT/SE99/01270, published as WO 00/03991, which applications disclosed the utility of these compounds for the treatment of diseases resulting from autoimmunity, such as multiple sclerosis, insulin-dependent diabetes mellitus, systemic lupus erythematosus, rheumatoid arthritis, inflammatory bowel disease and psoriasis and, furthermore, diseases where pathologic inflammation plays a major role, such as asthma, atherosclerosis, stroke and Alzheimer's disease.

Processes for preparing therapeutically active quinoline carboxamides also have been described in International Application No. PCT/SE2003/000780, published as WO 03/106424 and in International Application No. PCT/EP2011/061490, published as WO 2012/004338. A deuterated form of a quinoline carboxamide is described in International Application No. PCT/EP2012/061798, published as WO 2012/175541.

Pharmaceutical compositions containing a salt of a quinoline carboxamide having enhanced stability during long-term storage at room temperature, methods for the manufacture of such compositions, crystalline salts of quinoline carboxamides and methods for preparing crystalline salts of quinoline carboxamides are described in the International Application No. PCT/EP2005/050485, published as WO 2005/074899.

The use of various quinoline carboxamides for the treatment of cancer, more particularly solid cancers, such as prostate cancer and breast cancer, was disclosed in International Application No. PCT/SE00/02055, published as WO 01/30758. It has been found that these compounds bind to and inhibit the interactions of an immunomodulatory protein (S100A9), which protein promotes tumor development, influences suppressive and pro-angiogenic cells in the tumor microenvironment and participates in the establishment of pre-metastatic niches.

The general term "cancer" covers a large number of malignant diseases, which may be classified in two ways: by the type of tissue in which the cancer originates (histological type) and by primary site, or the location in the body where the cancer first developed. The international standard for the classification and nomenclature of histologies is the International Classification of Diseases for Oncology, Third Edition (ICD-O-3). From a histological standpoint the cancers may be grouped into six major categories, viz. carcinoma, sarcoma, myeloma, leukemia, lymphoma and so-called mixed types.

It is now a well-established fact that angiogenesis plays an important role in the growth, progression and metastasis of solid tumors (Joyce J. A. et al., Nature Reviews Cancer 9, 239-252 (April 2009)). For example, tasquinimod, which has been shown to be a potent anti-angiogenic agent (Isaacs J. et al., Prostate 66: 1768-1778, 2006), is currently in phase III clinical development for oral treatment of castrate resistant prostate cancer (CRPC) metastatic to the bone.

Hematological malignancies are cancer types affecting blood, bone marrow, and lymph nodes. In contrast to solid tumors, hematological malignancies are generally not considered dependent on angiogenesis for disease progression.

Hematological malignancies may derive from either of the two major blood cell lineages: myeloid and lymphoid cell lines. The myeloid cell line normally produces granulocytes, erythrocytes, thrombocytes, macrophages, and mast cells, whereas the lymphoid cell line produces B, T, NK and plasma cells. Lymphomas (e.g. Hodgkin's Lymphoma), lymphocytic leukemias, and myeloma are derived from the lymphoid line, while acute and chronic myelogenous leukemia (AML, CML), myelodysplastic syndromes and myeloproliferative diseases are myeloid in origin. As blood, bone marrow, and lymph nodes are intimately connected through the immune system, a disease affecting one haematological system may affect the two others as well.

Leukemia is part of a broader group of neoplasms which affect the blood, bone marrow, and lymphoid system, known as tumors of the hematopoietic and lymphoid tissues. In leukemia the bone marrow high numbers of abnormal white blood cells are produced in the bone marrow, called blasts or leukemia cells. In 2012, leukemia developed in 352,000 people globally and caused 265,000 deaths.

The four main types of leukemia are acute lymphoblastic leukemia (ALL), acute myeloid leukemia (AML), chronic lymphocytic leukemia (CLL) and chronic myeloid leukemia (CML). There are also some less common forms of leukemias, not belonging to any of the aforementioned main types.

ALL is the most common type of leukemia in young children, but also affects adults, especially elderly people. Standard treatments involve chemotherapy and radiotherapy. Subtypes include precursor B acute lymphoblastic leukemia, precursor T acute lymphoblastic leukemia, Burkitt's leukemia, and acute biphenotypic leukemia.

CLL most often affects adults over the age of 55, mainly men. An aggressive subtype of CLL is B-cell prolymphocytic leukemia. Hairy cell leukemia (HCL) also is sometimes considered a subtype of CLL.

AML too occurs more commonly in men than women. Except for the subtype acute promyelocytic leukemia (APL), which has a five-year survival of over 90%, the five-year survival rate in AML is as low as 40%. Subtypes of AML, other than acute promyelocytic leukemia, are acute myeloblastic leukemia, and acute megakaryoblastic leukemia.

Treatment modes for hematological malignancies often involve the use of conventional chemotherapeutic agents, such as Chlorambucil, Cyclophosphamide, Vincristine etc., generally in multi-drug treatment regimes with other types of medications, such as antimetabolite drugs or corticosteroids, or in combination with irradiation and/or bone marrow transplantation. Furthermore, tyrosine kinase inhibitors such as imatinib are being used for the treatment of leukemia, primarily CLL. However, there remains a need for further treatment options.

Roquinimex (Linomide), 4-hydroxy-N, 1-dimethyl-2-oxo-N-phenyl-1,2-dihydroquinoline-3-carboxamide, has been investigated for use in the treatment of various cancer diseases, including hematological malignancies.

Thus, in Bone Marrow Transplant. 2000 June; 25(11): 1121-7 a study is reported where 278 AML patients received either Roquinimex 0.2 mg/kg body weight or placebo twice weekly for 2 years following autologous bone marrow transplantation (ABMT). Surviving patients were followed for up to 6.9 years. However, the study showed no benefit for Roquinimex over placebo regarding relapse or survival following ABMT for AML in remission.

In Cancer Immunol Immunother. 2002 December; 51 (11-12): 596-602, the effect of Roquinimex was investigated in BALB/c mice inoculated with B-cell leukemia (BCL1) cells and it was found that the compound had no impact on graft survival or graft versus leukemia (GVL) effects.

Thus the quinoline carboxamide Roquinimex had been tested for use in the treatment of leukemia, but had been found ineffective. In fact, in a book titled Biotic Type Antioxidants: The Prospective Search Area for Novel Chemical Drugs (VSP BV, 2000; ISBN 90-6764-308-4), the anti-angiogenic based effect of Roquinimex is mentioned as a possible explanation for the lack of activity of the compound against leukemia.

The international application WO 2012/175541 (vide supra) mentions that deuterated Tasquinimod is useful for the treatment of various malignant hyperproliferative diseases or autoimmune diseases. While leukemia is mentioned as one such disease, no data is provided for this disease. On the other hand, it is noted that the compound is capable of inhibiting prostate tumor growth via a mechanism involving an anti-angiogenic response.

SUMMARY OF THE INVENTION

The present inventors now have found that a compound of formula (I) as defined herein shows a surprisingly beneficial effect against leukemia, in particular acute leukemia. Thus, provided herein is a compound of formula (I)

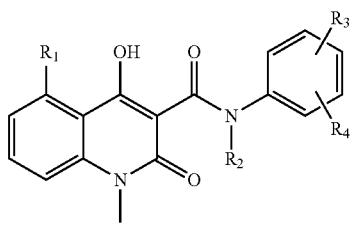

(I)

or a pharmaceutically acceptable salt thereof,
wherein
$R_1$ is selected from H, methyl, ethyl, n-propyl, iso-propyl, methoxy, ethoxy, fluoro, chloro, bromo, trifluoromethyl, and trifluoromethoxy;
$R_2$ is C1-C4 alkyl;
$R_3$ is selected from methyl, methoxy, fluoro, chloro, bromo, trifluoromethyl, and trifluoromethoxy;
$R_4$ is selected from hydrogen, fluoro and chloro, with the proviso that $R_4$ is selected from fluoro and chloro only when $R_3$ is selected from fluoro and chloro;
for use in the treatment of leukemia.

In some embodiments, the treatment is performed by administration to a mammal subject, such as a human, of an amount of from 0.001 mg to 0.2 mg of the compound of formula (I)/kg of body weight per day, or of a corresponding amount of a pharmaceutically acceptable salt thereof.

Preferably, the administration is oral, but it also may be e.g. rectal, or parenteral, e.g. by injection, such as subcutaneous, intramuscular or intravenous injection.

In some embodiments, the treatment further comprises radiation therapy. In some embodiments, the treatment further comprises stem cell transplantation.

In a second aspect, the use of the compound of formula (I) or a pharmaceutically acceptable salt thereof is provided, for the manufacturing of a medicament for the treatment of leukemia.

Another aspect is a method of treatment of leukemia comprising administering to a mammal subject, in particular a human subject, in need of such treatment, a therapeutically effective amount of a compound of formula (I) or a pharmaceutically acceptable salt thereof.

In some embodiments, the compound of formula (I) is 4-hydroxy-5-methoxy-N, 1-dimethyl-2-oxo-N-[4-(trifluoromethyl)phenyl]-1,2-dihydroquinoline-3-carboxamide (tasquinimod) or a pharmaceutically acceptable salt thereof.

DETAILED DESCRIPTION OF THE INVENTION

Definitions

Figure 1:
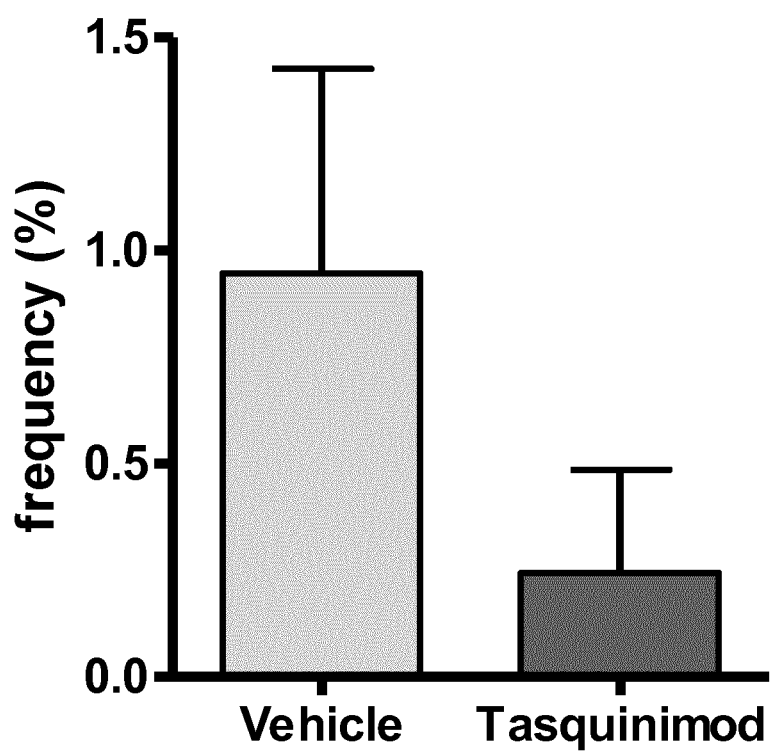
FIG. 1 is a diagram showing the frequency of tumor cells in bone marrow for mice in a control group (n=11) treated with vehicle only, and for mice in a group treated with tasquinimod (n=14).

For the purpose of the present invention the term leukemia generally refers to any of the various types and subtypes of leukemia, i.e. lymphoblastic leukemia (ALL), acute myeloid leukemia (AML), chronic lymphocytic leukemia (CLL) and chronic myeloid leukemia (CML), and any subtype of these, as well as any of the other, less common types of leukemia.

"Optional" or "optionally" means that the subsequently described event or circumstance may but need not occur, and that the description includes instances where the event or circumstance occurs and instances in which it does not.

"Pharmaceutically acceptable" means that which is useful in preparing a pharmaceutical composition that is generally safe, non-toxic, and neither biologically nor otherwise undesirable and includes that which is acceptable for veterinary use as well as human pharmaceutical use.

Examples of pharmaceutically acceptable salts comprise salts with (as counter ion) an alkali metal ion, e.g. $Li^+$, $Na^+$ or $K^+$, or with an alkaline earth ion, e.g. $Mg^{2+}$ or $Ca^{2+}$, or with any other pharmaceutically acceptable metal ion, e.g. $Zn^{2+}$ or $Al^{3+}$; or pharmaceutically acceptable salts formed with organic bases, such as diethanolamine, ethanolamine, N-methylglucamine, triethanolamine or tromethamine.

"Therapeutically effective amount" means an amount of a compound of formula (I) or a pharmaceutically salt thereof, that, when administered to a subject for treating a disease state (here: leukemia), is sufficient to effect such treatment for the disease state. The "therapeutically effective amount" will vary depending on e.g. the age and relative health of the treated subject, the state of progression of the leukemia, the route and form of administration, the possible additional use of other drugs, e.g. in a combination therapy, etc.

As used herein the terms "treatment" or "treating" is an approach for obtaining beneficial or desired results including clinical results. Beneficial or desired clinical results can include, but are not limited to, alleviation or amelioration of one or more symptoms of leukemia ("the disease"), diminishment of extent of the disease, stabilization (i.e., not worsening) of the state of the disease, preventing spread of the disease, delay or slowing of progression of the disease, amelioration or palliation of the disease state, and remission (whether partial or total), whether detectable or undetectable. The term can also mean prolonging survival as compared to expected survival without the treatment.

Symptoms of leukemia include fatigue, malaise, loss of appetite, weight loss, fever, anemia, bleeding, frequent infections, vomiting, headache, sore throat, night sweats, bone or joint pain, enlarged lymph nodes in the neck, underarm, groin or above the collarbone, abdominal discomfort or feeling of fullness, vision problems, sores in the eyes, and swelling of the testicles.

The term "mammal" refers to a human or any mammalian animal, e.g. a primate, a farm animal, a pet animal, or a laboratory animal. Preferably, the mammal is a human.

The mammal (e.g. human) subject that may suitably be treated according to the present invention may be one suffering from leukemia, or one at (increased) risk of developing leukemia.

The term "C1-C4 alkyl" refers to a branched or unbranched alkyl group having from 1, 2, 3 or 4 carbon atoms, i.e. methyl, ethyl, n-propyl, isopropyl, n-butyl, sec-butyl, isobutyl or tert-butyl.

The term methoxy refers to the moiety MeO—, or $CH_3O$—.

The term ethoxy refers to the moiety EtO—, or $CH_3CH_2O$—.

The terms fluoro, chloro and bromo also may be represented by F, Cl and Br.

The term trifluoromethyl refers to the moiety $CF_3$—.

The term trifluoromethoxy refers to the moiety $CF_3O$—.

As noted herein above, the compound for use according to the invention is a compound of formula (I)

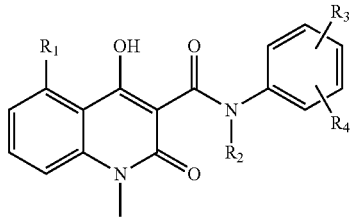

(I)

or a pharmaceutically acceptable salt thereof, as defined herein above.

In the compound of formula (I), $R_1$ is selected from H, methyl, ethyl, n-propyl, iso-propyl, methoxy, ethoxy, fluoro, chloro, bromo, trifluoromethyl, and trifluoromethoxy. In some embodiments, $R_1$ is selected from methyl, ethyl, n-propyl, iso-propyl, methoxy, ethoxy, fluoro, chloro, bromo, trifluoromethyl, and trifluoromethoxy. In some other embodiments, $R_1$ is selected from ethyl, n-propyl, iso-propyl, methoxy, ethoxy, chloro, bromo, trifluoromethyl, and trifluoromethoxy. In still other embodiments, $R_1$ is selected from ethyl, methoxy, chloro, and trifluoromethyl. In some particular embodiments, $R_1$ is methoxy.

The moiety $R_2$ is a C1-C4 alkyl radical, which radical may be branched or linear. In some embodiments, $R_2$ is a C1-C3 alkyl radical. In some embodiments, $R_2$ is methyl or ethyl. In some particular embodiments, $R_2$ is methyl.

The moiety $R_3$ is selected from methyl, methoxy, fluoro, chloro, bromo, trifluoromethyl, and trifluoromethoxy. In some embodiments, $R_3$ is selected from methyl, methoxy, fluoro, chloro, trifluoromethyl, and trifluoromethoxy. In some particular embodiments, $R_3$ is trifluoromethyl.

$R_4$ is selected from hydrogen, fluoro and chloro, with the proviso that $R_4$ is selected from fluoro and chloro only when $R_3$ is selected from fluoro and chloro. In some embodiments, $R_4$ is hydrogen or fluoro. In some particular embodiments, $R_4$ is hydrogen.

In some particular embodiments, in a compound of formula (I),
$R_1$ and $R_4$ are as defined herein above;
$R_2$ is methyl or ethyl, in particular methyl; and
$R_3$ is selected from methyl, methoxy, fluoro, chloro, trifluoromethyl, and trifluoromethoxy.

In some other particular embodiments, in a compound of formula (I),
$R_1$ is as defined herein above;
$R_2$ is methyl or ethyl, in particular methyl;
$R_3$ is selected from methyl, methoxy, fluoro, chloro, trifluoromethyl, and trifluoromethoxy; and
$R_4$ is H.

In some embodiments, $R_3$ is in para-position, i.e. the compound for use as defined herein may be represented by formula (Ia)

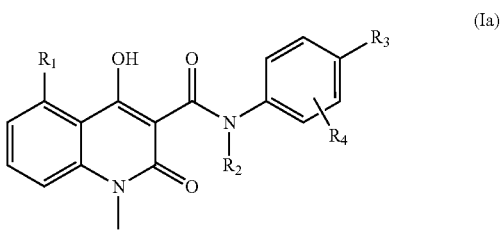

(Ia)

wherein $R_1$, $R_2$, $R_3$ and $R_4$ are as defined herein above.

For example, in some embodiments of a compound of formula (Ia),
$R_1$ and $R_4$ are as defined herein above;
$R_2$ is methyl or ethyl, in particular methyl; and
$R_3$ is selected from methyl, methoxy, fluoro, chloro, trifluoromethyl, and trifluoromethoxy.

In some other particular embodiments, in a compound of formula (Ia),
$R_1$ is as defined herein above;
$R_2$ is methyl or ethyl, in particular methyl;
$R_3$ is selected from methyl, methoxy, fluoro, chloro, trifluoromethyl, and trifluoromethoxy; and
$R_4$ is H.

As noted herein above, in some embodiments, $R_4$ is hydrogen. In those embodiments, the compound of formula (I) may be represented by formula (Ib)

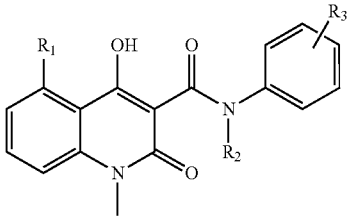

(Ib)

wherein $R_1$, $R_2$ and $R_3$ are as defined herein above.

For example, in some embodiments of a compound of formula (Ib), $R_2$ is methyl or ethyl, in particular methyl;

$R_3$ is selected from methyl, methoxy, fluoro, chloro, trifluoromethyl, and trifluoromethoxy; and $R_1$ is as defined herein above.

In some particular embodiments of a compound of formula (I), $R_3$ is in para-position and $R_4$ is H, and the compound for use as defined herein may then be represented by formula (Ic)

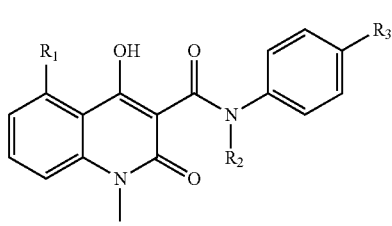

(Ic)

wherein $R_1$, $R_2$ and $R_3$ are as defined herein above.

In some particular embodiments of a compound of formula (Ic), $R_2$ is methyl or ethyl, in particular methyl;

$R_3$ is selected from methyl, methoxy, fluoro, chloro, trifluoromethyl, and trifluoromethoxy; and $R_1$ is as defined herein.

For the purpose of the present invention, any reference to a compound of formula (I) also should be understood as a reference to a compound of any one of the formulas (Ia), (Ib) and (Ic), unless otherwise specified or apparent from the context.

In one embodiment, the compound of formula (I) is 4-hydroxy-5-methoxy-N,1-dimethyl-2-oxo-N-[4-(trifluoromethyl)phenyl]-1,2-dihydroquinoline-3-carboxamide (tasquinimod), of the structural formula:

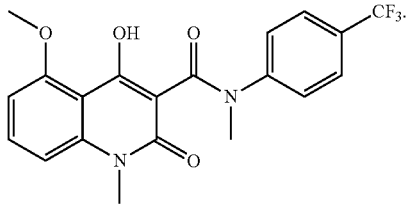 [SMILES: COc1cccc2c1c(O)c(C(=O)N(C)c1ccc(C(F)(F)F)cc1)c(=O)n2C]

As mentioned herein above, compounds of formula (I), pharmaceutically acceptable salts thereof, deuterated forms thereof, crystalline salts thereof, and pharmaceutical compositions containing the compounds and their salts, as well as methods for preparing such compounds, their salts, deuterated forms and pharmaceutical compositions containing the compounds and their salts have been described in WO 99/55678, WO 00/03991, WO 03/106424, WO 2005/074899, WO 2012/004338 and WO 2012/175541 (vide supra), which documents are hereby incorporated by reference in their entireties into the present application.

In some embodiments, any reference to a compound of formula (I) also encompasses the deuterated form of thereof. As mentioned herein above, a deuterated form of tasquinimod is described in WO 2012/175541. The person of ordinary skill in the art will be capable of preparing analogously deuterated compounds of formula (I) by following the description of in said WO pamphlet. In some embodiments, thus, the compound of formula (I) has a deuterium enrichment in the moiety $R_2$ of formula (I) of at least 70%, more preferably at least 90%. For example, in some embodiments, $R_2$ is methyl having a deuterium enrichment of at least 70%, more preferably at least 90%.

In some particular embodiments, the compound of formula (I) is tasquinimod having a deuterium enrichment in the amide-N methyl group of at least 70%, more preferably at least 90%.

In some other embodiments, the compound of formula (I) is non-deuterated, having a deuterium content corresponding to the natural abundance of deuterium.

The present invention includes the compound of formula (I) or a pharmaceutically acceptable salt thereof, formulated in a pharmaceutical composition a pharmaceutically acceptable salt thereof, optionally together with a pharmaceutically acceptable excipient, e.g. a carrier, for use in the treatment of leukemia.

The leukemia may be any type of leukemia, e.g. a leukemia belonging to any of the four main groups or not.

In some embodiments, the leukemia is an acute leukemia. In some other embodiments, the leukemia is a chronic leukemia.

In some embodiments, the leukemia is a myeloid leukemia. In some other embodiments, the leukemia is a lymphocytic or lymphoblastic leukemia.

In some embodiments, the leukemia is acute lymphoblastic leukemia. In some embodiments, the leukemia is acute myeloid leukemia. In some embodiments, the leukemia is chronic lymphocytic leukemia. In some embodiments, the leukemia is chronic myeloid leukemia.

The pharmaceutical composition may be suitable for enteral administration, such as rectal or oral administration, or for parenteral administration to a mammal (especially a human), and comprises a therapeutically effective amount of a compound of formula (I) or a pharmaceutically acceptable salt thereof, as active ingredient, optionally in association with a pharmaceutically acceptable excipient, e.g. a pharmaceutically acceptable carrier. The therapeutically effective amount of the active ingredient is as defined herein above and depends e.g. on the species of mammal, the body weight, the age, the individual condition, individual pharmacokinetic data, and the mode of administration.

For enteral, e.g. oral, administration, the compounds of formula (I) may be formulated in a wide variety of dosage forms. The pharmaceutically acceptable carriers may be either solid or liquid. Solid form preparations include powders, tablets, pills, lozenges, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well-known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

Exemplary compositions for rectal administration include suppositories which can contain, for example, a suitable non-irritating excipient, such as cocoa butter, synthetic glyceride esters or polyethylene glycols, which are solid at ordinary temperatures, but liquefy and/or dissolve in the rectal cavity to release the drug.

The compound of formula (I) also may be administered parenterally, e.g. by injection or infusion, e.g. by intravenous, intraarterial, intraosseous, intramuscular, intracerebral, intracerebroventricular, intrasynovial, intrasternal, intrathecal, intralesional, intracranial, intratumoral, intracutaneous and subcutaneous injection or infusion. Thus, for parenteral administration, the pharmaceutical compositions may be in the form of a sterile injectable or infusible preparation, for example, as a sterile aqueous or oleaginous suspension. This suspension may be formulated according to techniques known in the art using suitable dispersing or wetting agents (e.g., Tween 80), and suspending agents. The sterile injectable or infusible preparation may also be a sterile injectable or infusible solution or suspension in a non-toxic parenterally acceptable diluent or solvent. For example, the pharmaceutical composition may be a solution in 1,3-butanediol. Other examples of acceptable vehicles and solvents that may be employed in the compositions of the present invention include, but are not limited to, mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant.

Solutions for parenteral use also may contain suitable stabilizing agents, and if necessary, buffer substances. Suitable stabilizing agents include antioxidizing agents, such as sodium bisulfate, sodium sulfite or ascorbic acid, either alone or combined, citric acid and its salts and sodium EDTA. Parenteral solutions may also contain preservatives, such as benzalkonium chloride, methyl- or propyl-paraben, and chlorobutanol.

Conventional procedures for the selection and preparation of suitable pharmaceutical formulations are described, for example, in "Pharmaceutics—The Science of Dosage Form Design", M. B. Aulton, Churchill Livingstone, $2^{nd}$ ed. 2002 (ISBN 0443055173, 9780443055171). Suitable pharmaceutical excipients, e.g. carriers, and methods of preparing pharmaceutical dosage forms also are described in Remington's Pharmaceutical Sciences, Mack Publishing Company, a standard reference text in art of drug formulation.

The pharmaceutical compositions may comprise from approximately 1% to approximately 95%, preferably from approximately 20% to approximately 90% of a compound of formula (I), together with at least one pharmaceutically acceptable excipient. In general, the compounds of formula (I) will be administered in a therapeutically effective amount by any of the accepted modes of administration for agents that serve similar utilities.

While e.g. injection or rectal administration of a compound of formula (I) may be contemplated if necessary, oral administration generally is considered the most convenient.

The dosage level and frequency will generally be as determined by the treating physician, with due regard to factors such as and the sex, age, corporal weight and relative health of the treated subject, the state of progression of the leukemia, the selected route and form of administration, the additional use of other drugs, e.g. in a combination therapy.

Generally, a daily dosage ranging from a minimum of 0.001 mg/kg body weight, or 0.002 mg/kg body weight or 0.005 mg/kg body weight or 0.01 mg/kg body weight, to a maximum of 0.2 mg/kg body weight, or 0.1 mg/kg body weight, or 0.05 mg/kg body weight, or 0.02 mg/kg body weight is contemplated.

In one embodiment, the compound of formula (I) is administered in an amount of 0.05 to 0.15 mg/day, or 0.08 to 0.1 mg/day, e.g. 0.1 mg/day.

In one embodiment, the compound of formula (I) is administered in an amount of 0.1 to 0.3 mg/day, or 0.15 to 0.25 mg/day, e.g. 0.2 mg/day.

In one embodiment, the compound of formula (I) is administered in an amount of 0.1 to 1 mg/day, or 0.2 to 0.8 mg/day, e.g. 0.5 mg/day.

In one embodiment, the compound of formula (I) is administered in an amount of 0.2 to 1.5 mg/day, or 0.4 to 1.2 mg/day, e.g. 0.8 mg/day.

In one embodiment, the compound of formula (I) is administered in an amount of 0.5 to 2 mg/day, or 0.8 to 1.2 mg/day, e.g. 1 mg/day.

In one embodiment, the compound of formula (I) is administered in an amount of 0.8 to 3 mg/day, or 1 to 2.5 mg/day, e.g. 2 mg/day.

In one embodiment, the compound of formula (I) is administered in an amount of 1 to 6 mg/day, or 2 to 4 mg/day, e.g. 3 mg/day.

In some embodiments, the dosage may be gradually adjusted to reach optimal results, so-called dosage titration. For example, dosage titration may comprise starting with a low daily dosage of e.g. 0.25 mg and maintaining this dose level for a period of 1 or 2 weeks. In case no significant side effects are encountered that may contraindicate raising the dose, the level may then be increased, e.g. to 0.5 mg/day for 1 or 2 weeks, after which period another increase may be contemplated, to reach a daily dosage of 1 mg, and so on. In such a method, if any significant side effects occur after an incremental increase of the dosage, the dosage may again be reduced to a previous level.

Side effects that may occur include those that may generally be encountered in this type of treatment, e.g. gastrointestinal problems, tiredness, and flu-like syndrome, considered to be related to dosage.

The compound of formula (I) preferably is administrated on a daily basis, e.g. 1-3 times a day, or 1-2 times a day, such as once daily. In some embodiments, the drug is administrated on a less frequent basis, e.g. every two days, once a week etc.

It should also be noted that if a pharmaceutically acceptable salt of the compound of formula (I) is administered, an equivalent dosage would be one resulting in the indicated dosage of the compound in non-salt form.

The above information and embodiments generally also apply to pharmaceutically acceptable salts of the compound of formula (I), unless otherwise specifically indicated or apparent from the context.

EXAMPLES

Herein below the invention will be further illustrated by a number of non-limiting examples. wherein tasquinimod is be tested in three different murine xenograft acute leukemia models.

Example 1

Acute Myeloid Leukemia (AML)

U937 model—Ten million U937 cells (Monocytic human cell line, ATCC® CRL-1593.2TM) were injected i.v. in the tail vein of female C.B.-17 SCID mice. The mice were then randomly distributed into groups of 10-14 mice and received treatment with vehicle or tasquinimod ad lib in the drinking water. One group of mice was treated with tasquinimod 30 mg/kg/day and one group of mice was treated with vehicle, starting on the day of injection of U937 cells. The groups were terminated on day 21, before clinical signs of the tumor burden, and the tumor burden was analyzed in bone marrow by flow cytometry using a fluorochrome labeled anti-human CD45 antibody. The frequency of tumor cells found in bone marrow, in the tasquinimod treated group (n=14) and in the control group (n=1), respectively, is shown in FIG. 1.

Example 2

Acute Lymphocytic Leukemia (ALL)

Figure 2:
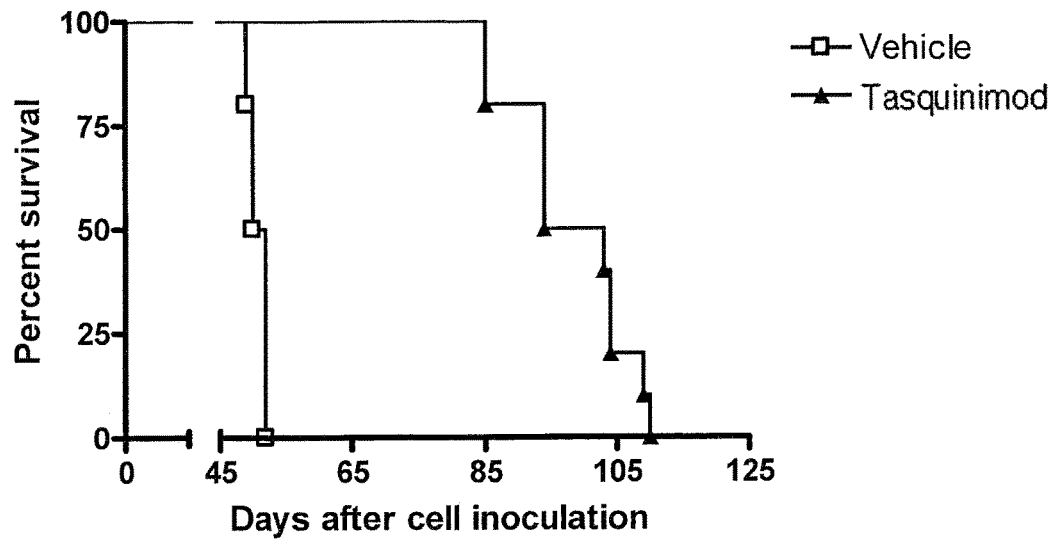
FIG. 2 is a graph showing the percent survival as a function of days after inoculation, of mice inoculated with human ALL cells and treated with either vehicle only or with Tasquinimod, 30 mg/kg.
Figure 3:
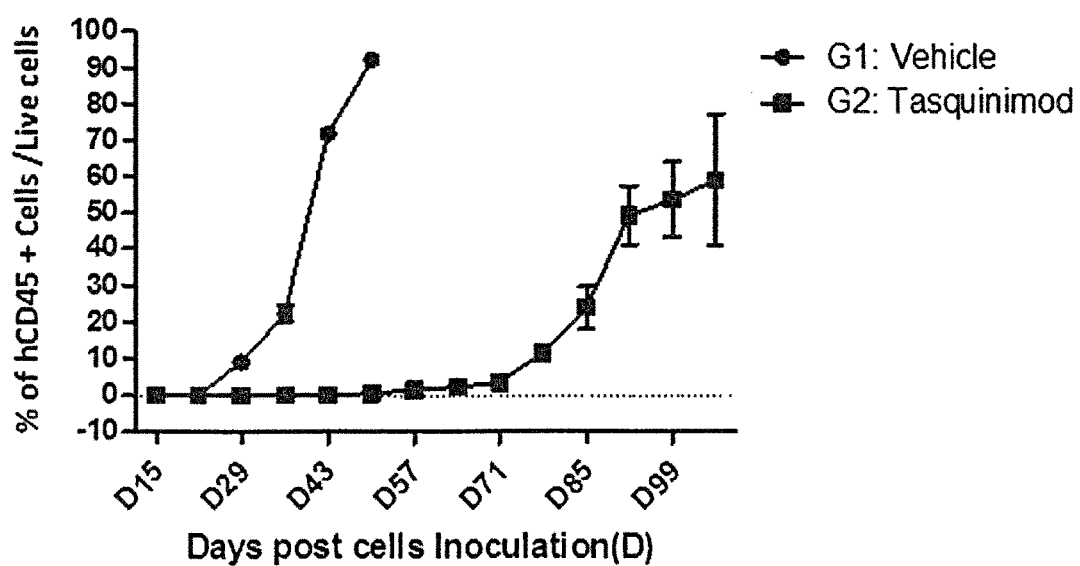
FIG. 3 is a graph showing the tumor burden growth, as a function of days after inoculation, of mice inoculated with human ALL cells, and treated with vehicle only or with Tasquinimod 30 mg/kg.

Tasquinimod was tested in a Patient Derived Xenograft (PDX) model AL-7015 provided by Crown Bioscience In. (www.crownbio.com). Cells derived from a patient with B-cell ALL were used. On Day 0, NOD/SCID mice were inoculated i.v. with $70 \times 10^6$ AL-7015-P2 leukemic cells per mouse. From day 1 to termination mice were treated with tasquinimod ad lib. in the drinking water at 30 mg/kg. Mice were terminated, as soon as any sign of morbidity was observed. The median survival time for the vehicle group was 51 days, while it was 99 days for the treatment group ($p<0.0001$) (FIG. 2). In the treatment group, the tumor burden remained close to zero for at least 10 weeks, long after the vehicle group had reached 100% tumor burden (FIG. 3).

The invention claimed is:

1. A method of treatment of leukemia selected from acute lymphoblastic leukemia and acute myeloid leukemia, by administering 4-hydroxy-5-methoxy-N,1-dimethyl-2-oxo-N-[4-(trifluoromethyl)phenyl]-1,2-dihydroquinoline-3-carboxamide (tasquinimod) or a pharmaceutically acceptable salt thereof to a mammal in need thereof.

2. The method according to claim 1, wherein the treatment is by administration of an amount of from 0.001 mg to 0.2 mg of the compound/kg of body weight per day, or of a corresponding amount of the pharmaceutically acceptable salt.

3. The method according to claim 1, wherein the treatment is by administration of the compound or salt 1-3 times a day.

4. The method according to claim 1, wherein the compound or salt is administered dissolved or suspended in a liquid vehicle.

5. The method according to claim 1, wherein the treatment further comprises radiation therapy and/or autologous stem cell transplantation.

6. The method according to claim 1, wherein the leukemia is acute lymphoblastic leukemia.

7. The method according to claim 1, wherein the leukemia is acute myeloid leukemia.

8. The method according to claim 1, wherein the mammal is a human.

9. The method according to claim 1, wherein the treatment is by oral administration.

10. The method according to claim 9, wherein the treatment is by administration of an amount of from 0.001 mg to 0.2 mg of the compound/kg of body weight per day, or of a corresponding amount of the pharmaceutically acceptable salt.

11. The method according to claim 9, wherein the treatment is by administration of the compound or salt 1-3 times a day.

12. The method according to claim 9, wherein the compound or salt is administered in a solid or semi-solid dosage form.

13. The method according to claim 12, wherein the solid or semi-solid dosage form is a capsule, a tablet or a pill.

14. The method according to claim 9, wherein the compound or salt is administered dissolved or suspended in a liquid vehicle.

15. The method according to claim 9, wherein the treatment further comprises radiation therapy and/or autologous stem cell transplantation.

16. The method according to claim 9, wherein the leukemia is acute lymphoblastic leukemia.

17. The method according to claim 9, wherein the leukemia is acute myeloid leukemia.

18. The method according to claim 9, wherein the mammal is a human.

* * * * *